(12) United States Patent
Natanzon et al.

(10) Patent No.: US 8,601,385 B2
(45) Date of Patent: Dec. 3, 2013

(54) ZERO PIXEL TRAVEL SYSTEMS AND METHODS OF USE

(75) Inventors: Alexander Natanzon, Upper Saddle River, NJ (US); Andrei Leontiev, South Burlington, VT (US)

(73) Assignee: General Electric Company, Schenectady, NY (US)

( * ) Notice: Subject to any disclaimer, the term of this patent is extended or adjusted under 35 U.S.C. 154(b) by 820 days.

(21) Appl. No.: 12/277,931

(22) Filed: Nov. 25, 2008

(65) Prior Publication Data

US 2010/0131890 A1 May 27, 2010

(51) Int. Cl.
*G06F 3/048* (2013.01)
*G06F 3/01* (2006.01)

(52) U.S. Cl.
USPC ........... 715/769; 715/767; 715/778; 715/788; 715/802; 715/818

(58) Field of Classification Search
USPC ................ 715/767, 769, 778, 788, 802, 818
See application file for complete search history.

(56) References Cited

U.S. PATENT DOCUMENTS

| | | | | |
|---|---|---|---|---|
| 6,016,438 A * | 1/2000 | Wakayama | | 600/410 |
| 6,108,573 A * | 8/2000 | Debbins et al. | | 600/410 |
| 6,111,573 A * | 8/2000 | McComb et al. | | 715/763 |
| 6,182,127 B1 * | 1/2001 | Cronin et al. | | 709/219 |
| 6,510,459 B2 * | 1/2003 | Cronin et al. | | 709/219 |
| 7,034,860 B2 * | 4/2006 | Lia et al. | | 348/14.09 |
| 7,417,644 B2 * | 8/2008 | Cooper et al. | | 345/619 |
| 7,624,355 B2 * | 11/2009 | Baneth | | 715/802 |
| 8,112,712 B2 * | 2/2012 | Matsumoto | | 715/732 |
| 2004/0230940 A1 * | 11/2004 | Cooper et al. | | 717/100 |
| 2005/0015729 A1 * | 1/2005 | Fernandez et al. | | 715/765 |
| 2005/0091596 A1 * | 4/2005 | Anthony et al. | | 715/712 |
| 2005/0228250 A1 * | 10/2005 | Bitter et al. | | 600/407 |
| 2005/0251021 A1 * | 11/2005 | Kaufman et al. | | 600/407 |
| 2006/0013462 A1 * | 1/2006 | Sadikali | | 382/132 |
| 2007/0101292 A1 * | 5/2007 | Kupka | | 715/810 |
| 2009/0199099 A1 * | 8/2009 | Girgensohn et al. | | 715/719 |

\* cited by examiner

*Primary Examiner* — Nicholas Augustine
(74) *Attorney, Agent, or Firm* — Hanley, Flight and Zimmerman, LLC

(57) ABSTRACT

Certain embodiments of the present invention provide systems and methods for image layout and display on a display such as a PACS workstation display. Certain embodiments provide a method for image layout on a display. The method includes detecting an event related to movement of an image for placement on a display. The method also includes overlaying a navigation grid on at least a portion of the display. The navigation grid includes one or more sections corresponding to sections for content on the display. The method further includes indicating a section of the grid into which the image is to be positioned. In addition, the method includes updating the display to reflect the position of the image.

21 Claims, 8 Drawing Sheets

ZERO PIXEL TRAVEL SYSTEMS AND METHODS OF USE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

Medical imaging devices now produce diagnostic images in a digital representation. The digital representation typically includes a two dimensional raster of the image equipped with a header including collateral information with respect to the image itself, patient demographics, imaging technology, and other data used for proper presentation and diagnostic interpretation of the image. Often, diagnostic images are grouped in series each series representing images that have some commonality and differ in one or more details. For example, images representing anatomical cross-sections of a human body substantially normal to its vertical axis and differing by their position on that axis from top (head) to bottom (feet) are grouped in so-called axial series. A single medical exam, often referred as a "study" or an "exam" typically includes one or more series of images, such as images exposed before and after injection of contrast material or images with different orientation or differing by any other relevant circumstance (s) of imaging procedure. The digital images are forwarded to specialized archives equipped with proper means for safe storage, search, access, and distribution of the images and collateral information for successful diagnostic interpretation.

When a user has many images to review and not enough real estate for displaying these images on a monitor, the user must drag images from the navigator to area on the monitor for large scale review. Such a manual approach requires a lot of mouse travel and user fatigue.

BRIEF SUMMARY OF THE INVENTION

Certain embodiments of the present invention provide systems and methods for image layout and display on a display such as a PACS workstation display.

Certain embodiments provide a method for image layout on a display. The method includes detecting an event related to movement of an image for placement on a display. The method also includes overlaying a navigation grid on at least a portion of the display. The navigation grid includes one or more sections corresponding to sections for content on the display. The method further includes indicating a section of the grid into which the image is to be positioned. In addition, the method includes updating the display to reflect the position of the image.

Certain embodiments provide an image layout and display system. The system includes a content display manager controlling content displayed for a user on a display, the content organized on the display according to one or more defined sections. The system also includes a navigator pane including a grid of one or more sections corresponding to the one or more defined sections of the display. The navigator pane appears based on user action with respect to displayed content and allows a user to select a section of the grid for positioning of content. An action in one of the navigator pane and the display translates into a corresponding action on the other of the navigator pane and the display. The content display monitor updates the content displayed to reflect the positioned content.

Certain embodiments provide a machine accessible medium having a set of instructions for execution on a processing device. The set of instructions execute a method for image navigation and display. The method includes detecting an event related to movement of an image for placement on a display. The method also includes overlaying a navigation grid on at least a portion of the display. The navigation grid includes one or more sections corresponding to sections for content on the display. The method further includes indicating a section of the grid into which the image is to be positioned. Additionally, the method includes updating the display to reflect the position of the image.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments relate to reading and interpretation of diagnostic imaging studies, stored in their digital representation and searched, retrieved, and read using a PACS and/or other clinical system. Certain embodiments provide ease of image layout on a display, as well as ease of propagating changes to derivative and related images also being displayed. Certain embodiments reduce an amount of mouse movement for image arrangement and display and simplify a reading workflow via an overlay grid.

In certain embodiments, images can be stored on a centralized server while reading is performed from one or more remote workstations connected to the server via electronic information links. Additionally, a single server often provides images for a plurality of workstations that can be connected through electronic links with different bandwidths.

Certain embodiments provide "smart" storage, transfer, usability and presentation of diagnostic images to help alleviate certain problems previously found in digital picture archiving and communication systems (PACS) including but not limited to: (1) a load on an information system, (2) a load on a network data transferring system, (3) heavy requirements to image content storage volume; and (4) latency time for image retrieval, image transmission, and image rendering on a diagnostic workstation's display. Additionally, certain embodiments help facilitate improved ergonomic screen layout, image manipulation, and image presentation for a diagnostic physician to provide more effective visual perception and diagnostic reading.

Certain embodiments provide systems and methods for transfer, improved storage, and improved presentation and perception of diagnostic images and other viewable media in order to help reduce system cost and complexity as well as physician waiting time and to help improve performance and work quality for a physician (and/or other workstation operator) to implement a workflow associated with reading, reviewing, and/or other utilization of the media.

Figure 1:
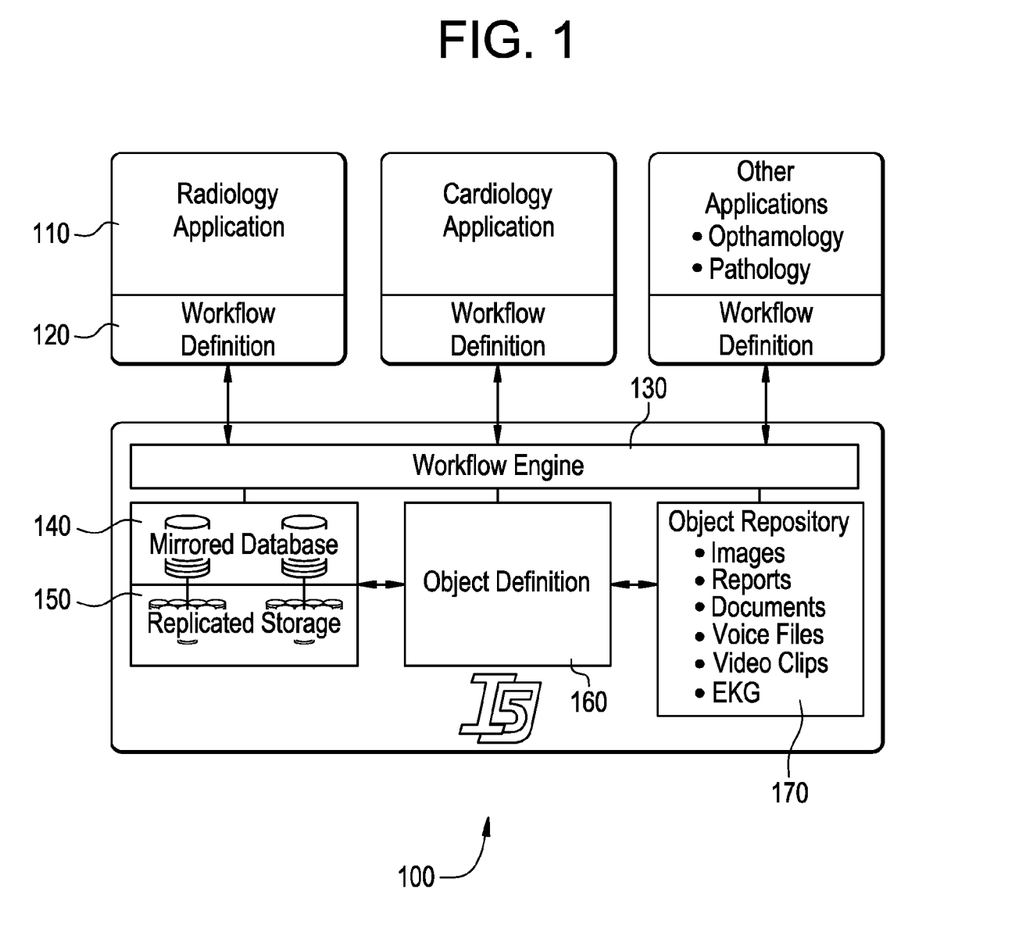
FIG. 1 demonstrates a business and application diagram for PACS information system in accordance with an embodiment of the present invention.

Certain embodiments provide an information system for a healthcare enterprise including a PACS system for radiology and/or other subspecialty system as demonstrated by the business and application diagram in FIG. 1. The system 100 of FIG. 1 includes a clinical application 110, such as a radiology, cardiology, ophthalmology, pathology, and/or application. The system 100 also includes a workflow definition 120 for each application 110. The workflow definitions 120 communicate with a workflow engine 130. The workflow engine 130 is in communication with a mirrored database 140, object definitions 60, and an object repository 170. The mirrored database 140 is in communication with a replicated storage 150. The object repository 170 includes data such as images, reports, documents, voice files, video clips, EKG information, etc.

Figure 2:
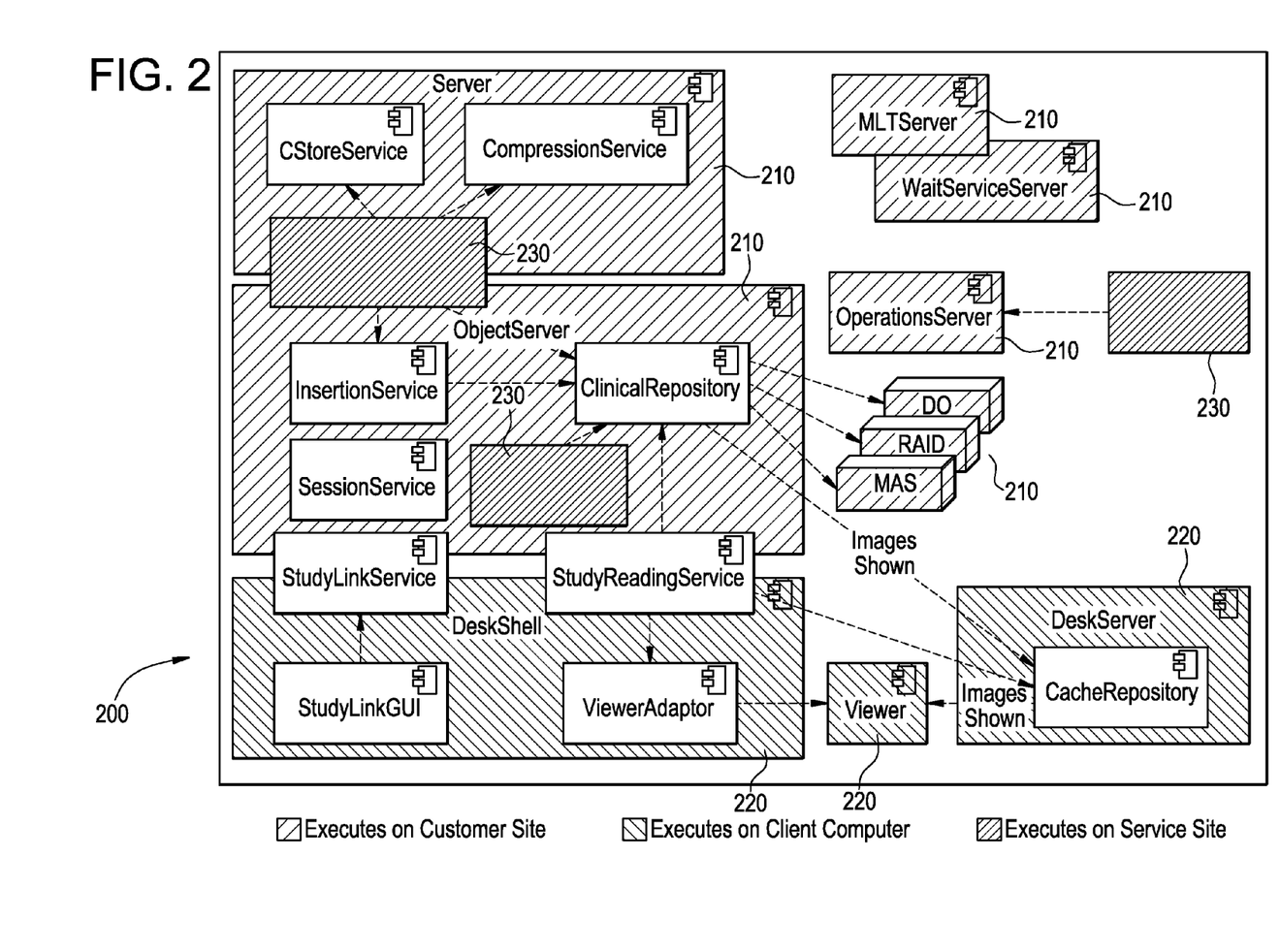
FIG. 2 illustrates an embodiment of an information system delivering application and business content in accordance with an embodiment of the present invention.

An embodiment of an information system that delivers application and business goals is presented in FIG. 2. The specific arrangement and contents of the assemblies constituting this embodiment bears sufficient novelty and constitute part of certain embodiments of the present invention. The information system 200 of FIG. 2 demonstrates services divided among a service site 230, a customer site 210, and a client computer 220. For example, a Dicom Server, HL7 Server, Web Services Server, Operations Server, database and other storage, an Object Server, and a Clinical Repository execute on a customer site 210. A Desk Shell, a Viewer, and a Desk Server execute on a client computer 220. A Dicom Controller, Compiler, and the like execute on a service site 230. Thus, operational and data workflow may be divided, and only a small display workload is placed on the client computer 220, for example.

Certain embodiments provide an architecture and framework for a variety of clinical applications. The framework can include front-end components including but not limited to a Graphical User Interface (GUI) and can be a thin client and/or thick client system to varying degree, which some or all applications and processing running on a client workstation, on a server, and/or running partially on a client workstation and partially on a server, for example.

Figure 3:
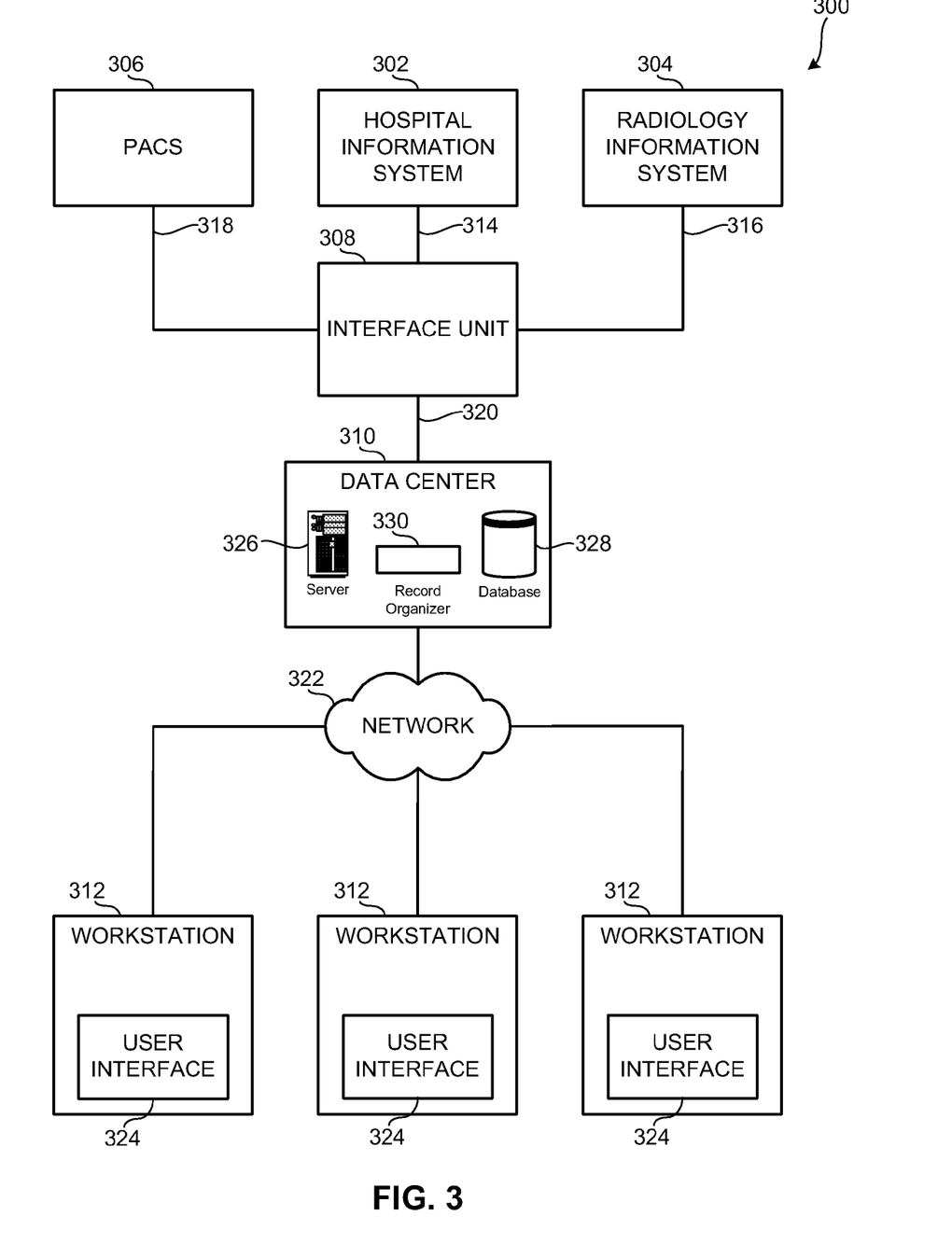
FIG. 3 illustrates a block diagram of an example clinical information system that may be used to implement systems and methods described herein.

FIG. 3 shows a block diagram of an example clinical information system 300 capable of implementing the example methods and systems described herein. The example clinical information system 300 includes a hospital information system ("HIS") 302, a radiology information system ("RIS") 304, a picture archiving and communication system ("PACS") 306, an interface unit 308, a data center 310, and a plurality of workstations 312. In the illustrated example, the HIS 302, the RIS 304, and the PACS 306 are housed in a healthcare facility and locally archived. However, in other implementations, the HIS 302, the RIS 304, and/or the PACS 306 may be housed one or more other suitable locations. In certain implementations, one or more of the PACS 306, RIS 304, HIS 302, etc., can be implemented remotely via a thin client and/or downloadable software solution. Furthermore, one or more components of the clinical information system 300 may be combined and/or implemented together. For example, the RIS 304 and/or the PACS 306 may be integrated with the HIS 302; the PACS 306 may be integrated with the RIS 304; and/or the three example information systems 302, 304, and/or 306 may be integrated together. In other example implementations, the clinical information system 300 includes a subset of the illustrated information systems 302, 304, and/or 306. For example, the clinical information system 300 may include only one or two of the HIS 302, the RIS 304, and/or the PACS 306. Preferably, information (e.g., scheduling, test results, observations, diagnosis, etc.) is entered into the HIS 302, the RIS 304, and/or the PACS 306 by healthcare practitioners (e.g., radiologists, physicians, and/or technicians) before and/or after patient examination.

The HIS 302 stores medical information such as clinical reports, patient information, and/or administrative information received from, for example, personnel at a hospital, clinic, and/or a physician's office. The RIS 304 stores information such as, for example, radiology reports, messages, warnings, alerts, patient scheduling information, patient demographic data, patient tracking information, and/or physician and patient status monitors. Additionally, the RIS 304 enables exam order entry (e.g., ordering an x-ray of a patient) and image and film tracking (e.g., tracking identities of one or more people that have checked out a film). In some examples, information in the RIS 304 is formatted according to the HL-7 (Health Level Seven) clinical communication protocol.

The PACS 306 stores medical images (e.g., x-rays, scans, three-dimensional renderings, etc.) as, for example, digital images in a database or registry. In some examples, the medical images are stored in the PACS 306 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 306 for storage. In some examples, the PACS 306 may also include a display device and/or viewing workstation to enable a healthcare practitioner to communicate with the PACS 306.

The interface unit 308 includes a hospital information system interface connection 314, a radiology information system interface connection 316, a PACS interface connection 318, and a data center interface connection 320. The interface unit 308 facilities communication among the HIS 302, the RIS 304, the PACS 306, and/or the data center 310. The interface connections 314, 316, 318, and 320 may be implemented by, for example, a Wide Area Network ("WAN") such as a private network or the Internet. Accordingly, the interface unit 308 includes one or more communication components such as, for example, an Ethernet device, an asynchronous transfer mode ("ATM") device, an 802.11 device, a DSL modem, a cable modem, a cellular modem, etc. In turn, the data center 310 communicates with the plurality of workstations 312, via a network 322, implemented at a plurality of locations (e.g., a hospital, clinic, doctor's office, other medical office, or terminal, etc.). The network 322 is implemented by, for example, the Internet, an intranet, a private network, a wired or wireless Local Area Network, and/or a wired or wireless Wide Area Network. In some examples, the interface unit 308 also includes a broker (e.g., a Mitra Imaging's PACS Broker) to allow medical information and medical images to be transmitted together and stored together.

In operation, the interface unit 308 receives images, medical reports, administrative information, and/or other clinical information from the information systems 302, 304, 306 via the interface connections 314, 316, 318. If necessary (e.g., when different formats of the received information are incompatible), the interface unit 308 translates or reformats (e.g., into Structured Query Language ("SQL") or standard text) the medical information, such as medical reports, to be properly stored at the data center 310. Preferably, the reformatted medical information may be transmitted using a transmission protocol to enable different medical information to share common identification elements, such as a patient name or social security number. Next, the interface unit 308 transmits the medical information to the data center 310 via the data center interface connection 320. Finally, medical information is stored in the data center 310 in, for example, the DICOM format, which enables medical images and corresponding medical information to be transmitted and stored together.

The medical information is later viewable and easily retrievable at one or more of the workstations 312 (e.g., by their common identification element, such as a patient name or record number). The workstations 312 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 312 receive commands and/or other input from a user via, for example, a keyboard, mouse, track ball, microphone, etc. As shown in FIG. 3, the workstations 312 are connected to the network 322 and, thus, can communicate with each other, the data center 310, and/or any other device coupled to the network 322. The workstations 312 are capable of implementing a user interface 324 to enable a healthcare practitioner to interact with the clinical information system 300. For example, in response to a request from a physician, the user interface 324 presents a patient medical history. Additionally, the user interface 324 includes one or more options related to the example methods and apparatus described herein to organize such a medical history using classification and severity parameters.

The example data center 310 of FIG. 3 is an archive to store information such as, for example, images, data, medical reports, and/or, more generally, patient medical records. In addition, the data center 310 may also serve as a central conduit to information located at other sources such as, for example, local archives, hospital information systems/radiology information systems (e.g., the HIS 302 and/or the RIS 304), or medical imaging/storage systems (e.g., the PACS 306 and/or connected imaging modalities). That is, the data center 310 may store links or indicators (e.g., identification numbers, patient names, or record numbers) to information. In the illustrated example, the data center 310 is managed by an application server provider ("ASP") and is located in a centralized location that may be accessed by a plurality of systems and facilities (e.g., hospitals, clinics, doctor's offices, other medical offices, and/or terminals). In some examples, the data center 310 may be spatially distant from the HIS 302, the RIS 304, and/or the PACS 306 (e.g., at General Electric® headquarters).

The example data center 310 of FIG. 3 includes a server 326, a database 328, and a record organizer 330. The server 326 receives, processes, and conveys information to and from the components of the clinical information system 300. The database 328 stores the medical information described herein and provides access thereto. The example record organizer 330 of FIG. 3 manages patient medical histories, for example. The record organizer 330 can also assist in procedure scheduling, for example.

Figure 4:
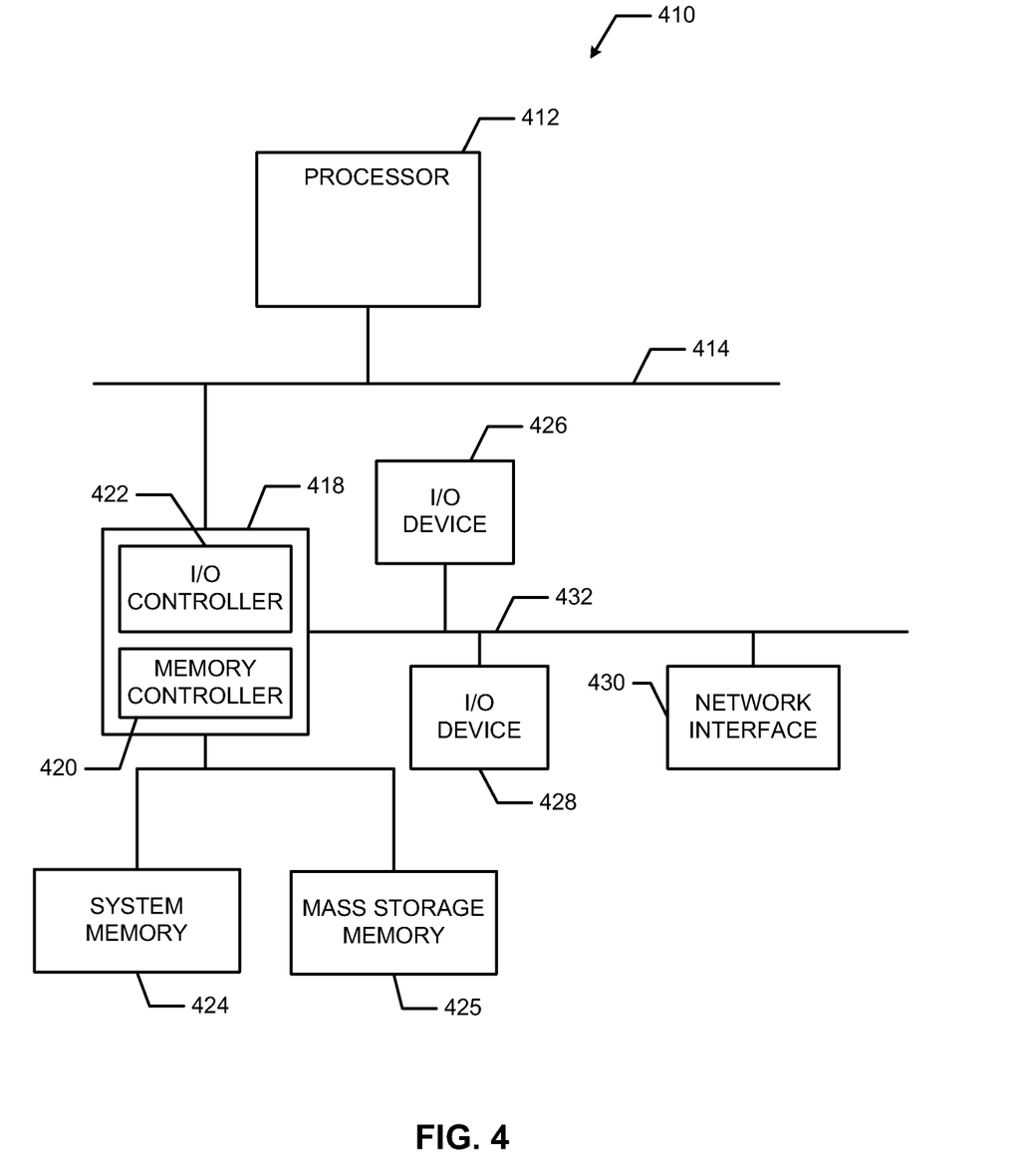
FIG. 4 shows a block diagram of an example processor system that may be used to implement systems and methods described herein.

FIG. 4 is a block diagram of an example processor system 410 that may be used to implement systems and methods described herein. As shown in FIG. 4, the processor system 410 includes a processor 412 that is coupled to an interconnection bus 414. The processor 412 may be any suitable processor, processing unit, or microprocessor, for example. Although not shown in FIG. 4, the system 410 may be a multi-processor system and, thus, may include one or more additional processors that are identical or similar to the processor 412 and that are communicatively coupled to the interconnection bus 414.

The processor 412 of FIG. 4 is coupled to a chipset 418, which includes a memory controller 420 and an input/output ("I/O") controller 422. As is well known, a chipset typically provides I/O and memory management functions as well as a plurality of general purpose and/or special purpose registers, timers, etc. that are accessible or used by one or more processors coupled to the chipset 418. The memory controller 420 performs functions that enable the processor 412 (or processors if there are multiple processors) to access a system memory 424 and a mass storage memory 425.

The system memory 424 may include any desired type of volatile and/or non-volatile memory such as, for example, static random access memory (SRAM), dynamic random access memory (DRAM), flash memory, read-only memory (ROM), etc. The mass storage memory 425 may include any desired type of mass storage device including hard disk drives, optical drives, tape storage devices, etc.

The I/O controller 422 performs functions that enable the processor 412 to communicate with peripheral input/output ("I/O") devices 426 and 428 and a network interface 430 via an I/O bus 432. The I/O devices 426 and 428 may be any desired type of I/O device such as, for example, a keyboard, a video display or monitor, a mouse, etc. The network interface 430 may be, for example, an Ethernet device, an asynchronous transfer mode ("ATM") device, an 802.11 device, a DSL modem, a cable modem, a cellular modem, etc. that enables the processor system 410 to communicate with another processor system.

While the memory controller 420 and the I/O controller 422 are depicted in FIG. 4 as separate blocks within the chipset 418, the functions performed by these blocks may be integrated within a single semiconductor circuit or may be implemented using two or more separate integrated circuits.

According to certain embodiments considered as examples in the present application, media files imported from a medical imaging device into a PACS are optionally subjected to a layered incremental compression. Certain media files are grouped in sequences called series, and certain series are grouped into studies, where each study represents a total set of media associated with a single medical exam. Each such study can be optionally attributed to a study type, where each study type is associated with a certain protocol for study interpretation. The protocol can include but is not limited to an order and positions for series display, configuration of a toolbar, annotation and measuring tools, and/or other data required for more efficient presentation of diagnostic images and rendering of a diagnosis. The set of tools and resources is referred to as a "study layout."

For each study registered in the database, an algorithm is used to create a list of respective series and individual images included in the study and selection of a proper layout for study display. Upon getting a request for study display, the server first generates comprehensive lists of media files to be used for reading the study and a related layout for study display. These lists are transferred to a client workstation and copies are kept on the server. According to the generated list of media files and a chosen layout for their presentation on the client workstation, a plan for transferring and optional processing and/or decompression of the media files is built and coordinated between client and server.

According to that plan, a first batch of media transfer includes a minimum amount of compression layers to deliver a coarse enough representation of the image(s) provided such that the coarse representation, while not suitable for diagnostic reading, is sufficient for navigating between the images to review the whole study and then focus on images with high diagnostic value. Upon presentation of the images on the diagnostic or other workstation, tools are offered to an operator for implementation of a diagnostic workflow or other relevant workflow. For example, tools can include but are not limited to: scrolling through the stack of images, adjusting brightness/contrast of the images, making measurements and annotations of the images, rendering some other representation(s) such as three-dimensional (3D) or oblique slicing, dictation and reporting tools, and/or other relevant tools.

Certain embodiments are described with respect to utilization of layered compression and related diagnostics. Certain embodiments can also apply to information and archiving systems used for storage of uniform data or for different types of data and media. Certain embodiments can apply to information systems wherein one of the targets of the information system is delivery of stored data to an application for interactive handling, subsequently referred to as "reading," and implemented though a reading computer application. Reading can be implemented according to a plurality of different scenarios or workflows further referred as "reading workflows." Each workflow can involve a different nature of the data set available for reading application. The data set can include data of the same type or of multiple types. Different types of data for each workflow can be of different volume and can be used at different stages of the reading workflow.

The loading plan can also include, for example, a description of what data should be available on a client workstation at any stage of the reading workflow in accordance with its normal implementation or in reaction to interactive actions of the operator. The description can specify data that should be delivered to the workstation for implementation of the next stages of the reading workflow upon most probable interactive interventions of the operator, for example.

Delivery engines and other hardware/software can be arranged in a delivery chain to provide sequential delivery of data or its usable pieces through a chain of information subsystems from original data storage to the client workstation in accordance with the loading plan.

The loading plan and delivery chain can identify that the reading workflow has proceeded to a next step due to a progression of events and/or in response to human interaction. Missing data pieces for a next step of the reading workflow are identified, and missing data information is broadcast to all or selected delivery components. For example, delivery hardware and/or software impacted by the missing data are notified about the missing information.

Loading plans governing sequential actions of delivery components can be reconciled in accordance with proceeding to a next stage of the reading workflow and accounting for the missing data. Reconciliations of the loading plans of different delivery elements are coordinated to help reduce or eliminate data traffic congestions through the delivery chain.

Load on components of the delivery chain(s) that serve several data destinations can be balanced through partitioning between the destinations so that data traffic to all destinations of the same data delivery component is in proportion to a bandwidth of a link between the delivery components and in proportion to a capacity of each data destination to receive and process incoming data and/or data pieces.

Thus, certain embodiments provide a PACS configured for importing, storage, access, distribution, and/or interpretation of radiological exams presented as a plurality of digital images and other diagnostic data including but not limited to textual, visual, audio, graphical, and/or other types of data. The PACS can utilize a single data type and/or a combination of different data types with different scenarios for interpretation, management, and/or other functional purposes referred to as workflows, for example. The PACS includes delivery hardware for retrieval of data from physical storage, optional processing of the data, and transferring of the data to a client application. The client application can reside, for example, on the same hardware installation that includes an informational server and physical data storage or on a remote computer connected to the information system through a LAN, WAN, or Internet connection, for example.

The PACS includes one or more delivery engines or dedicated software objects/agents controlling delivery hardware components for delivery of digital data from storage to an end user. Delivery includes but is not limited to retrieval of the data from its original physical storage, optional transmission of the data through a LAN, WAN, Internet, or other connection, and optional compression/decompression or otherwise organized data processing on its way from original physical storage to the end-user client application, for example.

Delivery agents represented by delivery hardware and delivery engines can be optionally arranged in a chain of delivery nodes. Data used by some of delivery nodes for transfer or processing is provided to the delivery nodes by another delivery node called a source delivery node. Data processed or transferred by some other delivery node is used by a subsequent delivery node referred to as a sink delivery node for further transfer and/or processing, for example.

The PACS includes hardware and/or software for creation, storage, and/or modification of data lists including a description of a plurality of data types and a plurality of data objects that should be delivered to a workstation or server for implementation of a workflow. Data lists are retrievable in response to launching a workflow on a workstation or server. Data lists are implemented as explicit lists and/or graphs, recursive lists and/or graphs, on-the fly logical algorithms, and/or other representation, for example.

The PACS establishes one or more loading plans specifying a preferred priority or order for delivery of different objects referred to in a data list to a client/display workstation and/or server in accordance with an implementation of a workflow and/or in accordance with most probable deviations from a workflow implementation resulting from human interactions and/or other factor(s).

The PACS generates a node/engine loading plan for each delivery node/engine based on the general loading plan. The loading plan and/or plans serve as an operational algorithm for the delivery node/engine.

The PACS includes software and/or hardware for reconsideration and reconciliation of a general loading plan and node/engine loading plans for relevant delivery nodes/engines in response to proceeding to a next step of the workflow and/or changing of the workflow implementation, for example.

In certain embodiments, the PACS includes a general purpose compact or distributed information system designed and used for import, storage, and/or distribution of a uniform data type or data of different natures that includes usage data of a uniform type or a combination of data of different natures within different scenarios (e.g., workflows) of interpretation, management, and/or other functional purpose. The PACS includes delivery hardware for retrieval of data from physical storage, optional processing of the data, and transferring of the data to a client application, provided that the client application can reside either on the same hardware installation that includes an informational server and physical data storage or on remote computer connected to the information system through a LAN, WAN, Internet, and/or other data connection. The PACS includes one or more delivery engines—dedicated software objects/agents controlling delivery hardware component(s) for delivery of digital data from its original storage to an end user. Delivery includes but is not limited to retrieval of the data from its original physical storage, optional transmission of the data through LAN, WAN, Internet, and/or other connection, and optional compression/decompression or otherwise organized data processing as the data is on its way from original physical storage to the end-user application. Delivery agents represented by delivery hardware and delivery engines may be optionally arranged in a chain of delivery nodes such that data used by some delivery node(s) for transfer or processing is provided to the delivery node(s) by another delivery node called a source delivery node, while data processed or transferred by another delivery node is used by a subsequent delivery node called a sink delivery node for further transfer and/or processing. The PACS includes means for creation, storage, and modification of the data lists—a comprehensive description of plurality of data types and plurality of data objects that should be delivered to respective workstation or server for successful implementation of the workflow. The data lists are retrieval in response to launching any workflow on any workstation or server implemented either as explicit lists and/or graphs, recursive lists and/or graphs, on the fly logical algorithms, or other means most proper for any preferred embodiment of the invention. The PACS can establish one or more loading plans representing a preferred priority or order for the delivery of different objects referred to in the data list to respective workstation(s) and/or server(s) in accordance with an implementation of a workflow and/or in accordance with one or more most probable deviations from a normal workflow implementation resulting from human interactions and/or any other factors. The PACS generates a node/engine loading plan for each delivery node/engine based on the general loading plan. The loading plan and/or plans serve as an operational algorithm for a delivery node/engine. The PACS can facilitate reconsideration and reconciliation of the general loading plan and/or node/engine loading plans for all relevant delivery nodes/engines in response to a next step in the workflow and/or changing of the workflow implementation. The PACS can coordinate the loading plans for a plurality of delivery nodes/engines along the delivery chain to reduce data congestion along delivery chain. The PACS can synchronize reconciliation of the node loading plans between all delivery nodes serving a workflow. The PACS can adjust a priority, order, and/or speed of data retrieval, transfer, and/or processing by the delivery nodes/engines in response to an updated node loading plan.

Images and related data are displayed at a client workstation for radiologist and/or other clinician review. When a user has many images for review and not enough real estate for display of the images on a monitor, the user must drag images from the navigator to an area on the monitor for large scale review. Such a manual approach involves much mouse movement and user fatigue.

In certain embodiments, a review workstation display can be configured and divided into a plurality of segments or quadrants to display multiple images and/or other data. Images and/or other data can be placed in the segments of the display automatically based on certain parameters and/or based on user preference, for example. Software running on the workstation can keep track of how many segments have been created on the display and what content is displayed in which segment (if any). Software running on the workstation can interact in thick and/or thin client operation to retrieve images and/or other data locally and/or remotely for display in one or more segments, for example. Images and/or other data can be from the same and/or multiple modalities, for example.

Hanging protocols can be used to define an arrangement of images and/or other information on a display. A workflow may involve an overview set of images and more focused sets of images. The workflow may require stepping through various configurations of images. A typical workflow can be an array or sequence of hangings, for example. This sequence of hangings can be saved as one piece, which may not be convenient because each step can be part of multiple sequences. Therefore, certain embodiments allow creation of a hanging protocol and saving of all or part of the hanging protocol as a separate object. The hanging protocol can be saved on multiple levels (e.g., common, group, private) depending upon a level at which sharing of tools and information with other users is desired. Additionally, certain embodiments provide a layout editor that allows a user to select which hanging protocol(s) from a library the user wants to apply to a particular layout for a sequence. An alignment tool can be used to create the hanging protocols and separate the workspace into a set of rectangles or set of nested rectangles. A user can populate the workspace with a series by dragging thumbnails into the rectangles.

In certain embodiments, a user can set matching criteria directly when dragging and dropping series images into rectangles, rather than manually selecting the matching criteria (e.g., sequential, by description, by orientation, by modality, etc), and the matching criteria is displayed in conjunction with the image. Placeholders can be allocated for series, as well as any presentation object and for derived data. For example, a user and/or application can reserve a place for a navigator, key images, fused images (derived from original series), etc. When deriving an image, a user and/or application can specify what the sources should be and can specify what is important in the series (e.g., description, contrast flag, attenuation corrected, etc.). Placeholder behavior properties can also be specified (e.g., activated upon opening, run cine, specify frame rate, continuous/non-continuous in a certain direction, etc.). A mouse mode can be specified in the hanging protocol (scrolling, triangulation, magnify, etc.). Comparison hangings can be created. Comparison hangings can be created for multiple modalities. For example, a hanging protocol can be created for comparison between CT and MR images, and this hanging protocol will be applied automatically when a certain combination of studies is selected for display.

Suppose twelve images are in a study, but a layout has room for eight images. A layout can be created including a placeholder for an overview wherein an image not previously displayed is a candidate to display in that placeholder. Multiple overview placeholders can be specified, for example.

Additionally, an indicator can be provided to indicate whether a viewer has seen the images. For example, an image thumbnail can include a red rectangle indicating that the image has not been reviewed. A yellow triangle can indicate that the image has been partially been reviewed, for example. A green circle can indicate that the image has been reviewed, for example. Color and shape coding (e.g., for black and white monitors) can be used on the series and represented on both a thumbnail and a full image, for example.

Figure 5:
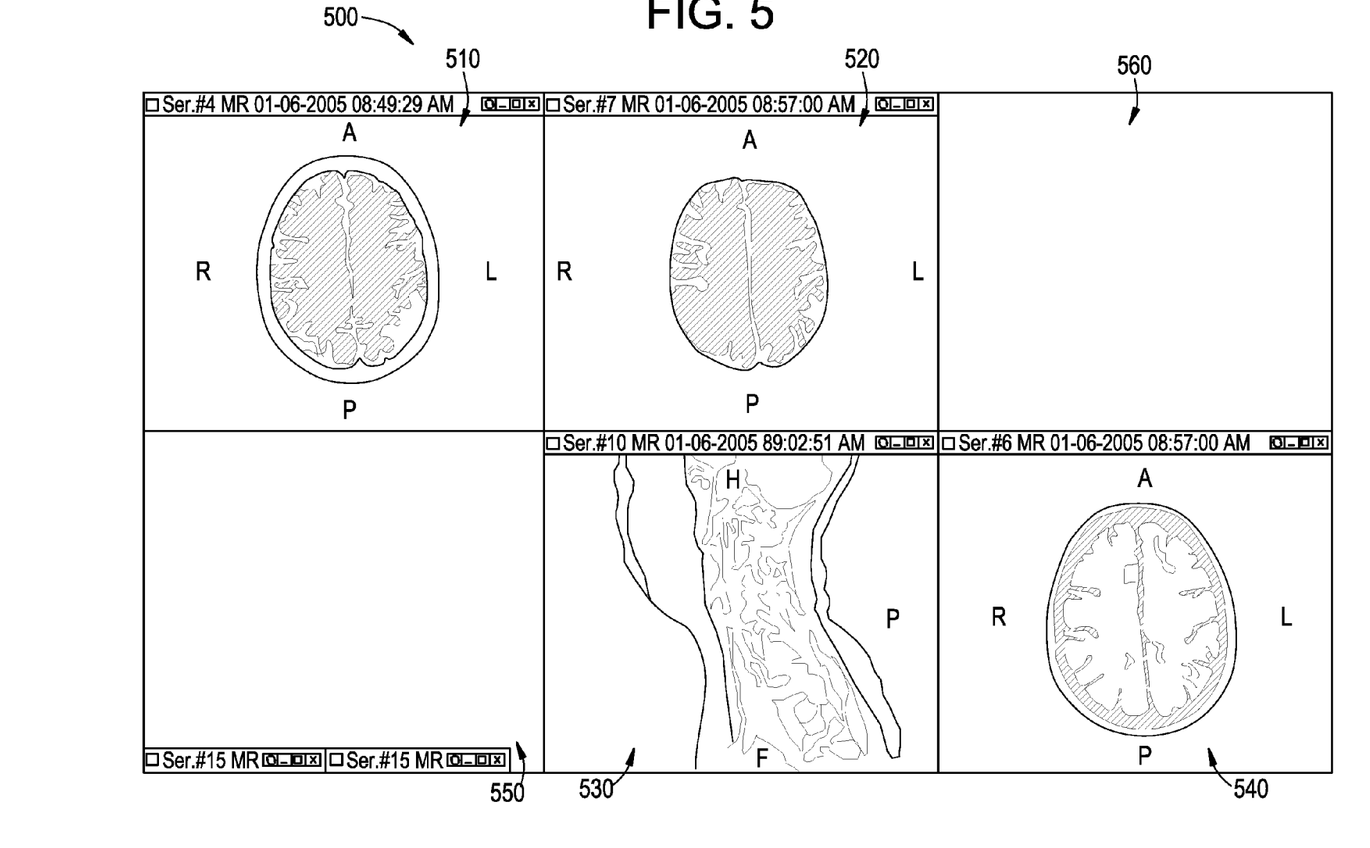
FIG. 5 shows an image viewing area of a workstation display divided into sections for placing images and/or other information in accordance with an embodiment of the present invention.

As shown, for example, in FIG. 5, an image viewing area 500 of a workstation display can be divided into six sections for placing images and/or other information. The example of FIG. 5 depicts four sections 510, 520, 530, 540 filed with images and two empty segments 550, 560. Additional images and/or other information can be placed in the empty segments 550, 560. Further, images and/or other information can be moved around among the segments 510, 520, 530, 540, 550, 560, for example. A plurality of images and other related information can be displayed to provide a reviewer with varying perspectives. For example, as shown in FIG. 5, a series of magnetic resonance (MR) images of a patient's brain, including diffusion and axial images, are provided in conjunction with a neck/spinal sagittal image for comparison and review.

In certain embodiments, the review workstation provides an overlay which simulates or represents the layout of the one or more connected monitors. The layout can include a grid or representation of sections of the display. The layout indicates which sections already include displayed images and/or other data and includes one or more placeholders representing vacant areas available for display. A user can drag one or more thumbnail images and/or other data into the placeholders to display that image and/or other data in the desired location on the monitor.

In one example, once a user starts dragging an image thumbnail, a layout navigator overlay grid appears, and the user can drop the thumbnail into a spot in the overlay grid. In another example, a certain key press or movement brings up the grid for positioning. A hashed or shaded grid sector may indicate that a sector is already occupied. A user can also drag and drop the image into an open sector without the application.

In one example, if a study includes three original series but has many empty placeholders, PACS viewing software can automatically reconstruct the missing images to fill in the empty placeholders on the display (i.e., derivative images). For example, a user can drag a series using a navigation pane to an empty space in the layout, and the PACS workstation will reconstruct the other derivative images based on the new series. Such positioning may be referred to herein as zero pixel travel to indicate a minimum amount of pixel movement to position an image in the layout. Thus, not only can the zero pixel travel navigation pane be used for placing an image series in a display layout, but also, if some placeholder includes a derivative of an image series, the derivatives can be updated as well based on the newly placed series. A derivative image can be derived based on one or more rules/algorithms, and those rules/algorithms can be automatically applied to the new series as laid out using the navigation pane.

Figure 6:
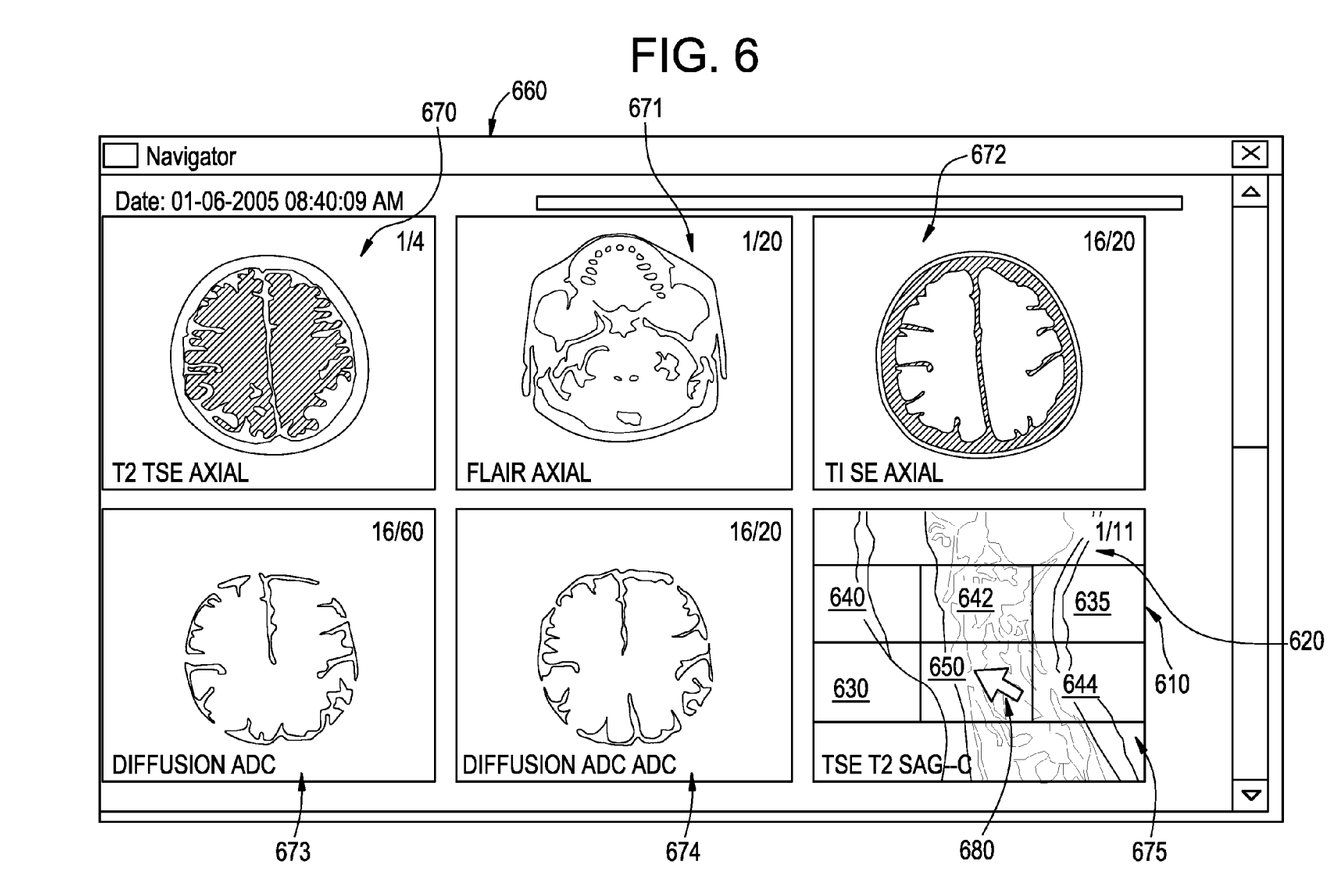
FIG. 6 shows a navigator pane with an overlay visualized over an image which was at an initial phase of user dragging on the display in accordance with an embodiment of the present invention.

As shown in FIG. 6, a navigator pane 610 is shown with an overlay visualized over an image 620 which was at an initial phase of user dragging on the display 660 (e.g., a few pixels). The navigator pane 610 includes a plurality of sections 630, 635, 640, 642, 644, 650 corresponding to a division of a display 660 into a plurality of sections 670-675. Overlay shading indicates a status of the screen placeholders. For example, as illustrated in FIG. 6, transparent sections 630, 635 indicate unused real estate; lightly shaded sections 640, 642, 644 indicate occupied placeholders; and heavily shaded sections 650 indicate a currently selected destination placeholder. The navigator pane 610 can be positioned at least partially over and/or adjacent to the image 620 and can provide at least some degree of transparency to view the image through the pane 610, for example. Using the cursor 680, a user can position content in the navigator pane 610 and, thus, on the display.

The displayed navigator pane overlay 610 interacts with program code and data to track which image(s) and/or other information are displayed in which locations on the monitor screen, as well as inter-dependencies and derivatives between displayed content in different locations, for example. In addition to facilitating ease of layout, the overlay grid 610 and supporting software help propagate changes in displayed content and layout to derivative and related images also being displayed.

Figure 7:
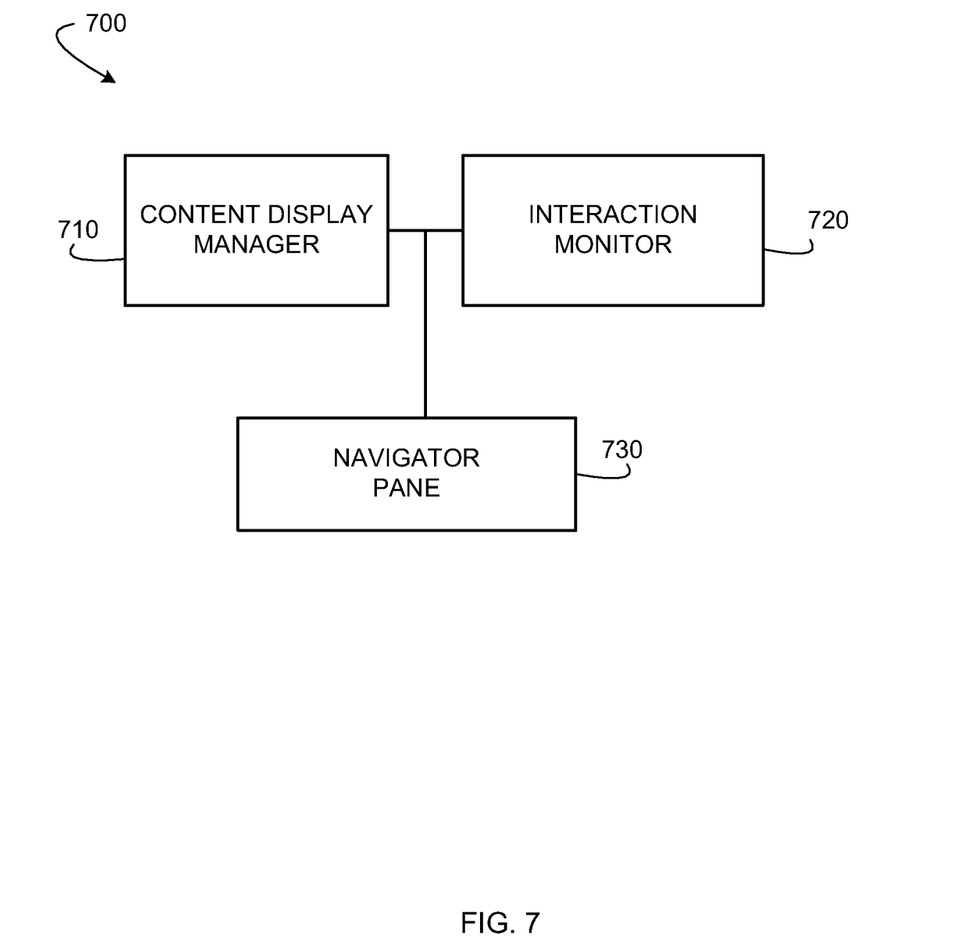
FIG. 7 illustrates a zero pixel travel system enabling a user to more easily navigate and position images and/or other data on a display with relatively little cursor movement in accordance with certain embodiments of the present invention.

FIG. 7 illustrates a zero pixel travel system 700 enabling a user to more easily navigate and position images and/or other data on a display with relatively little cursor movement (e.g., "zero" pixel travel) in accordance with certain embodiments of the present invention. The system 700 includes a content display manager 710, an interaction monitor 720, and a navigator pane 730. The content display manager 710 controls images and/or other information displayed on a workstation for user review. The interaction monitor 720 monitors user interaction with the workstation and with the content displayed. Upon entering a certain mode, for example, the interaction monitor 720 monitors cursor movement, mouse clicks, and cursor location on the workstation display. Such monitored action can trigger the appearance and use of the navigator pane 730. The navigator pane 730 includes one or more sections corresponding to a division of the display. The navigator pane 730 indicates which sections are occupied, unoccupied, reserved, and/or related (e.g., derivative, simulated, etc.), for example. An action in the navigator pane 730 translates into an action on the display and vice versa, for example.

For example, if a user initiates dragging an image to a location on the display, the interaction monitor 720 triggers the navigator pane 730 to appear. The user can then drop the image into a section of the navigator pane 730. As another example, a certain key press or movement of the cursor displays the navigator pane 730 for positioning. The navigator pane 730 can be overlaid on the display and include a certain degree of transparency to allow underlying images and/or other data on the display to continue to be seen by the user. A user can also drag and drop an image into an open section of the display without using the navigator pane 730, for example.

In certain embodiments, the content display manager 710, interaction monitor 720, and navigator pane 730 can work in conjunction with a hanging/display protocol and/or other user preference and/or system parameter, for example.

The content display manager 710, interaction monitor 720, and navigator pane 730 can be implemented in software, hardware, firmware, and/or a combination of these elements. The content display manager 710, interaction monitor 720, and navigator pane 730 can be implemented separately and/or combined in various forms. The content display manager 710, interaction monitor 720, and navigator pane 730 can be implemented as a set of instructions/routines forming machine executable code stored on a machine accessible medium for execution by a computing/processing device, for example.

Figure 8:
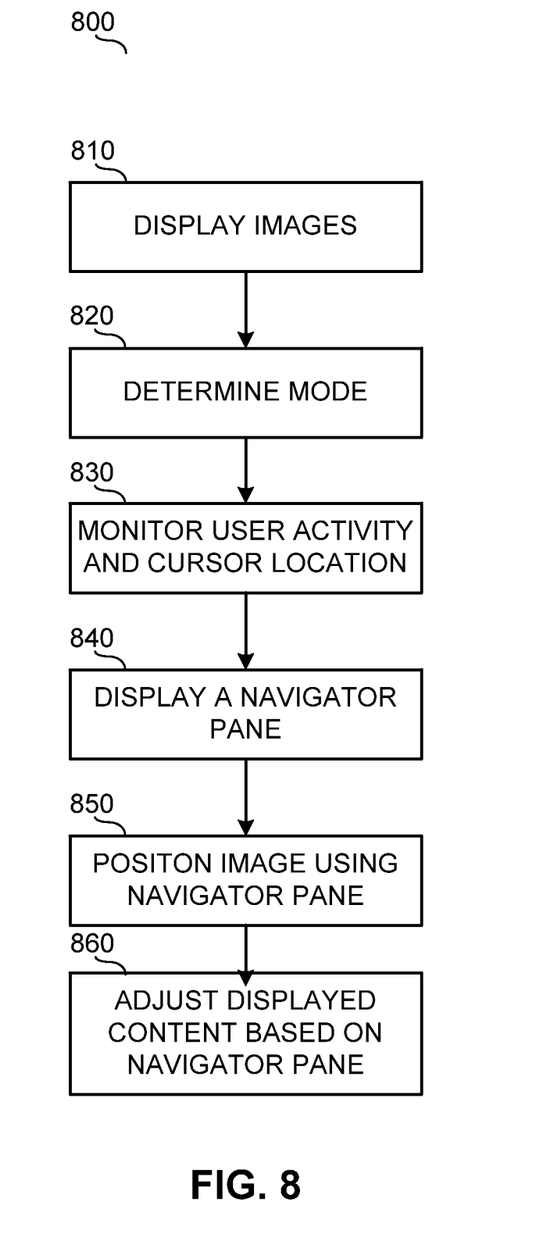
FIG. 8 illustrates a flow diagram for a method for positioning images and/or other data on a display in accordance with an embodiment of the present invention.

FIG. 8 illustrates a flow diagram for a method 800 for positioning images and/or other data on a display in accordance with an embodiment of the present invention. At 810, images and/or other information are displayed. For example, a series of computed tomography images are displayed in sections of a PACS workstation display.

At 820, entry into a certain mode, such as a navigation or layout mode, is determined. At 830, upon entering the certain mode, such as a navigation or layout mode, cursor movement, user activity (e.g., mouse clicks), and cursor location on the workstation display are monitored.

At 840, a navigator pane is displayed. For example, user/cursor action monitored above can trigger the appearance and use of the navigator pane. The navigator pane can include one or more sections corresponding to one or more sections dividing a display. The navigator pane indicates which sections of the display are occupied, unoccupied, reserved, and/or related (e.g., derivative, simulated, etc.), for example. The navigator pane may be a semi-transparent overlay on at least a portion of the display, for example. The navigator pane can appear in close proximity to an image being moved, for example. An action in the navigator pane translates into an action on the display and vice versa, for example.

For example, if a user initiates dragging an image to a location on the display, the navigator pane can be triggered to appear. As another example, a certain key press or movement of the cursor can display the navigator pane for positioning.

At 850, an image and/or other data is positioned in a section of the navigator pane. For example, a user can select an image to trigger the navigator pane to appear and can then select a section of the navigator pane to indicate a desired position for the image on the display.

At 860, displayed content is adjusted based on the content of the navigator pane. For example, if a user moved an image into a section of the navigator pane, the image is displayed in the corresponding section of the workstation display. Additionally, changes in displayed content and layout can be propagated to derivative and related images also being displayed.

One or more of the steps of the method 800 may be implemented alone or in combination in hardware, firmware, and/or as a set of instructions in software, for example. Certain examples may be provided as a set of instructions residing on a computer-readable medium, such as a memory, hard disk, DVD, or CD, for execution on a general purpose computer or other processing device.

Certain examples may omit one or more of these steps and/or perform the steps in a different order than the order listed. For example, some steps may not be performed in certain examples. As a further example, certain steps may be performed in a different temporal order, including simultaneously, than listed above.

Thus, certain embodiments provide for improved reading and interpretation of diagnostic imaging studies via a reviewing workstation, such as a PACS workstation. Certain embodiments provide a technical effect of user control over content layout on a display and improved ease of image layout, as well as ease of propagating changes to derivative and/or other related content also being displayed. Certain embodiments reduce an amount of mouse movement for image arrangement and display and simplify a reading workflow via an overlay grid.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for image layout on a display, said method comprising:
   detecting an event related to movement of an image for placement on a display;
   overlaying, in response to the detected event, a secondary interface including a navigation grid shown over at least a portion of a primary interface also shown on the display, the navigation grid including one or more sections representing and corresponding to sections of the display for positioning and display of content on the display, the navigation grid in the secondary interface separate from the display of content on the display in the primary interface and disappearing from the display after user interaction with the navigation grid;
   indicating, based on user selection, a section of the navigation grid into which the image is to be positioned; and
   updating the display with the image to reflect the position of the image based on user positioning of the image with respect to the navigation grid.

2. The method of claim 1, wherein a degree of overlay shading indicates a status of each section in the navigation grid.

3. The method of claim 2, wherein a transparent section of the navigation grid indicates an unused section of the display; a lightly shaded section of the navigation grid indicates an occupied section of the display; and a heavily shaded section of the navigation grid indicates a currently selected destination section for the image.

4. The method of claim 1, wherein detecting an event further comprises detecting a user dragging an image on the display, and wherein overlying a navigation grid further comprises displaying the grid and allowing the user to drag and drop the image into a section of the grid.

5. The method of claim 1, wherein the event comprises at least one of cursor movement and mouse click with respect to the image.

6. The method of claim 1, further comprising propagating content and layout changes for the display to a derivative image shown on the display.

7. The method of claim 6, wherein the derivative image is derived from one or more images or data according to a set of rules for display.

8. The method of claim 1, wherein indicating a section of the grid into which the image is to be positioned further comprises at least one of dragging and dropping the image into the section and selecting the section using the cursor.

9. An image layout and display system, said system comprising:

a processor and memory including computer program code which, when executed, is to implement:

a content display manager controlling content displayed for a user on a display, the content organized on the display according to one or more defined sections; and a navigator pane including a navigation grid of one or more sections representative of and corresponding to the one or more defined sections of the display, the navigator pane appearing on the display in a secondary interface overlaying at least a portion of a primary interface showing the content on the display, the navigator pane appearing based on user action with respect to displayed content and allowing a user to select a section of the navigation grid for positioning of content, the navigator pane with navigation grid in the secondary interface separate from the display of content on the display and disappearing from the display after user interaction with the navigation grid, wherein an action in one of the navigator pane and the display translates into a corresponding action on the other of the navigator pane and the display, and wherein the content display monitor updates the content displayed to reflect the positioned content based on user positioning of the content with respect to the navigation grid.

10. The system of claim 9, further comprising an interaction monitor monitoring user interaction with the displayed content and, upon entering a certain mode, monitors at least one of cursor movement, mouse clicks, and cursor location on the display to trigger the appearance and use of the navigator pane.

11. The system of claim 9, wherein the navigator pane indicates which sections of the display are occupied, unoccupied, reserved, and related.

12. The system of claim 11, wherein a degree of overlay shading indicates a status of each section in the navigation grid.

13. The system of claim 12, wherein a transparent section of the navigation grid indicates an unused section of the display; a lightly shaded section of the navigation grid indicates an occupied section of the display; and a heavily shaded section of the navigation grid indicates a currently selected destination section for the image.

14. The system of claim 9, wherein the content display monitor and the navigator pane propagate content and layout changes for the display to a derivative image shown on the display, wherein the derivative image is derived from other content displayed.

15. The system of claim 9, wherein the content display manager and the navigator pane operate in conjunction with a display protocol.

16. A machine accessible medium having a set of instructions for execution on a processing device, the set of instructions executing a method for image navigation and display, the method comprising:

detecting an event related to movement of an image for placement on a display;

overlaying, in response to the detected event, a secondary interface including a navigation grid shown over at least a portion of a primary interface also shown on the display, the navigation grid including one or more sections representing and corresponding to sections of the display for positioning and display of content on the display, the navigation grid in the secondary interface separate from the display of content on the display in the primary interface and disappearing from the display after user interaction with the navigation grid;

indicating, based on user selection, a section of the navigation grid into which the image is to be positioned; and updating the display with the image to reflect the position of the image based on user positioning of the image with respect to the navigation grid.

17. The machine accessible medium of claim 16, wherein a degree of overlay shading indicates a status of each section in the navigation grid.

18. The machine accessible medium of claim 17, wherein a transparent section of the navigation grid indicates an unused section of the display; a lightly shaded section of the navigation grid indicates an occupied section of the display; and a heavily shaded section of the navigation grid indicates a currently selected destination section for the image.

19. The machine accessible medium of claim 16, wherein detecting an event further comprises detecting a user dragging an image on the display, and wherein overlying a navigation grid further comprises displaying the grid and allowing the user to drag and drop the image into a section of the grid.

20. The machine accessible medium of claim 16, wherein the set of instructions further comprises propagating content and layout changes for the display to a derivative image shown on the display, wherein the derivative image is derived from one or more images and/or data according to a set of rules for display.

21. The machine accessible medium of claim 16, wherein indicating a section of the grid into which the image is to be positioned further comprises at least one of dragging and dropping the image into the section and selecting the section using the cursor.

* * * * *